(12) United States Patent
Suzuki

(10) Patent No.: US 6,885,725 B2
(45) Date of Patent: Apr. 26, 2005

(54) X-RAY IMAGE DIAGNOSIS APPARATUS

(75) Inventor: Katsumi Suzuki, Eirakudai (JP)

(73) Assignee: Hitachi Medical Corporation, Tokyo (JP)

(*) Notice: Subject to any disclaimer, the term of this patent is extended or adjusted under 35 U.S.C. 154(b) by 184 days.

(21) Appl. No.: 10/399,752

(22) PCT Filed: Oct. 25, 2001

(86) PCT No.: PCT/JP01/09405
§ 371 (c)(1),
(2), (4) Date: Apr. 22, 2003

(87) PCT Pub. No.: WO02/34135
PCT Pub. Date: May 2, 2002

(65) Prior Publication Data
US 2004/0022352 A1 Feb. 5, 2004

(30) Foreign Application Priority Data
Oct. 25, 2000 (JP) ........................................ 2000-325207

(51) Int. Cl.[7] .................................................. A61B 6/00
(52) U.S. Cl. ........................ 378/19; 378/98.8; 378/207
(58) Field of Search ....................... 378/19, 98.3, 98.8, 378/207; 250/370.08, 370.09, 370.11

(56) References Cited

U.S. PATENT DOCUMENTS 5,905,772 A 5/1999 Rutten ........................ 378/98.8

FOREIGN PATENT DOCUMENTS

JP 03-024492 A 2/1991
JP 10-186045 A 7/1998

Primary Examiner—Edward J. Glick
Assistant Examiner—Courtney Thomas
(74) Attorney, Agent, or Firm—Antonelli, Terry, Stout & Kraus, LLP

(57) ABSTRACT

Sensitivity information on the sensitivities of the channels of a flat x-ray detector (3) is used for sensitivity correction of an image formed by irradiation of a subject with x-rays and read out of the flat x-ray detector (3). The collection of sensitivity information is started when a signal for starting the collection of the sensitivity information is sent to a sensitivity information collection control means (11) from an operator console (12). The sensitivity information collection control means (11) sends an irradiation start signal for starting irradiation with calibration light to calibration light control means (10). The calibration light control means (10) controls calibration light irradiation means (9) so that a desired intensity of light may be applied to the inside of the flat x-ray detector (3). Thus, a calibration light reception signal outputted from the flat x-ray detector (3) is stored as sensitivity information in sensitivity information storage means (5). Consequently, such sensitivity information can be collected without irradiating the flat x-ray detector (3) with x-rays. Therefore, an x-ray image diagnosis apparatus in which the sensitivity information for correcting the sensitivities of the channels of the flat x-ray detector can be collected without irradiating the flat x-ray detector with x-rays is realized.

8 Claims, 3 Drawing Sheets

X-RAY IMAGE DIAGNOSIS APPARATUS

FIELD OF THE INVENTION

The present invention relates to an x-ray diagnosis apparatus which allows a sensitivity correction of an x-ray detector without irradiating x-rays on to the concerned x-ray detector.

BACKGROUND ART

One of conventional art flat X-ray detectors is, for example, disclosed in U.S. Pat. No. 5,905,772.

An x-ray image diagnosis apparatus making use of such as the above referred to flat x-ray detector generally receives with the flat x-ray detector transmitted x-rays which are obtained when x-rays from a x-ray generator are irradiated on to a subject and obtains an x-ray image using respective channel outputs from the flat x-ray detector as image information.

As the flat x-ray detector, one in which an x-ray fluorescent substance is laminated on arrays of photo detector elements, for example, one in which a scintillator is laminated on photo diode arrays such as amorphous silicons is used, however, the sensitivity of the respective channels in the detector elements differs each other.

For this reason, the sensitivity information of the respective channels were determined in advance, and when image taking, the outputs of the respective channels were individually corrected by making use of the sensitivity information.

Further, in order to obtain a further accurate correction image, the collection of the sensitivity information was performed at least once in a day and the sensitivity information was thus updated.

However, in the above conventional art, x-rays had to be irradiated on to the flat x-ray detector at a time other than image taking of a subject so as to collect the sensitivity information of the respective channels.

Since the sensitivity information collection through the x-ray irradiation requires to collect separate sensitivity information for plural image taking modes, it took about ten minutes at one time for collecting the required sensitivity information.

For this reason a possibility of exposure to operators in association with the sensitivity information collection increased, at the same time, during the sensitivity information collection other works in the concerned inspection room, for example, the preparation of the inspection were restricted, therefore, a problem was given rise which makes it difficult to immediately perform an image taking after the sensitivity information collection.

The present invention was carried out in view of the above situation and the object of the present invention is to realize an x-ray image diagnosis apparatus which permits to collect sensitivity information for performing sensitivity correction of respective channels without irradiating x-rays on to the flat x-ray detector.

SUMMARY OF THE INVENTION

In order to achieve the above object, the present invention is constituted as follows.

An x-ray image diagnosis apparatus which comprises an x-ray source for irradiating x-rays on to a subject, a flat x-ray detector disposed facing the x-ray source and including photo detection elements which convert x-rays transmitted through the subject in to light beams and detect the same, a flat x-ray detector control means which controls read out of an output from the flat x-ray detector, a sensitivity information memory means which memorizes an output from the flat x-ray detector as sensitivity information, and a sensitivity correction means which performs sensitivity correction of the image information read out from the flat x-ray detector by making use of the sensitivity information memorized in the sensitivity information memory means; further comprises means for irradiating light beams on to the photo detection elements in the flat x-ray detector and means for causing to memorize an output of the flat x-ray detector obtained in response to the irradiated light beams as sensitivity information in the sensitivity information memory means.

Thus, with the means for irradiating light beams on to the photo detection elements the sensitivity of the flat x-ray detector can be detected through irradiating x-rays on to the x-ray detection elements without using x-rays from the x-ray source.

Accordingly, an x-ray image diagnosis apparatus can be realized which permits to collect sensitivity information for correcting sensitivity of the flat x-ray detector without irradiating x-rays on to the flat x-ray detector.

Further, the present invention may further comprises a correction coefficient memory means which memorizes a correction coefficient for correcting the sensitivity information memorized in the sensitivity information memory means and a sensitivity information correction means which corrects the sensitivity information memorized in the sensitivity information memory means with the correction coefficient memorized in the correction coefficient memory means.

Thus, in a case when the amount of light beams from the light beam irradiation means is not uniformalized for all of the photo detection elements in the flat x-ray detector due to structural members inside the flat x-ray detector, through correcting non-uniformity of diffusive light beam amount with the sensitivity information correction means, an x-ray image diagnosis apparatus which permits to obtain an accurate sensitivity information can be realized.

PREFERRED EMBODIMENTS OF THE INVENTION

The embodiments of the x-ray image diagnosis apparatus according to the present invention will be explained with reference to the drawings.

Figure 1:
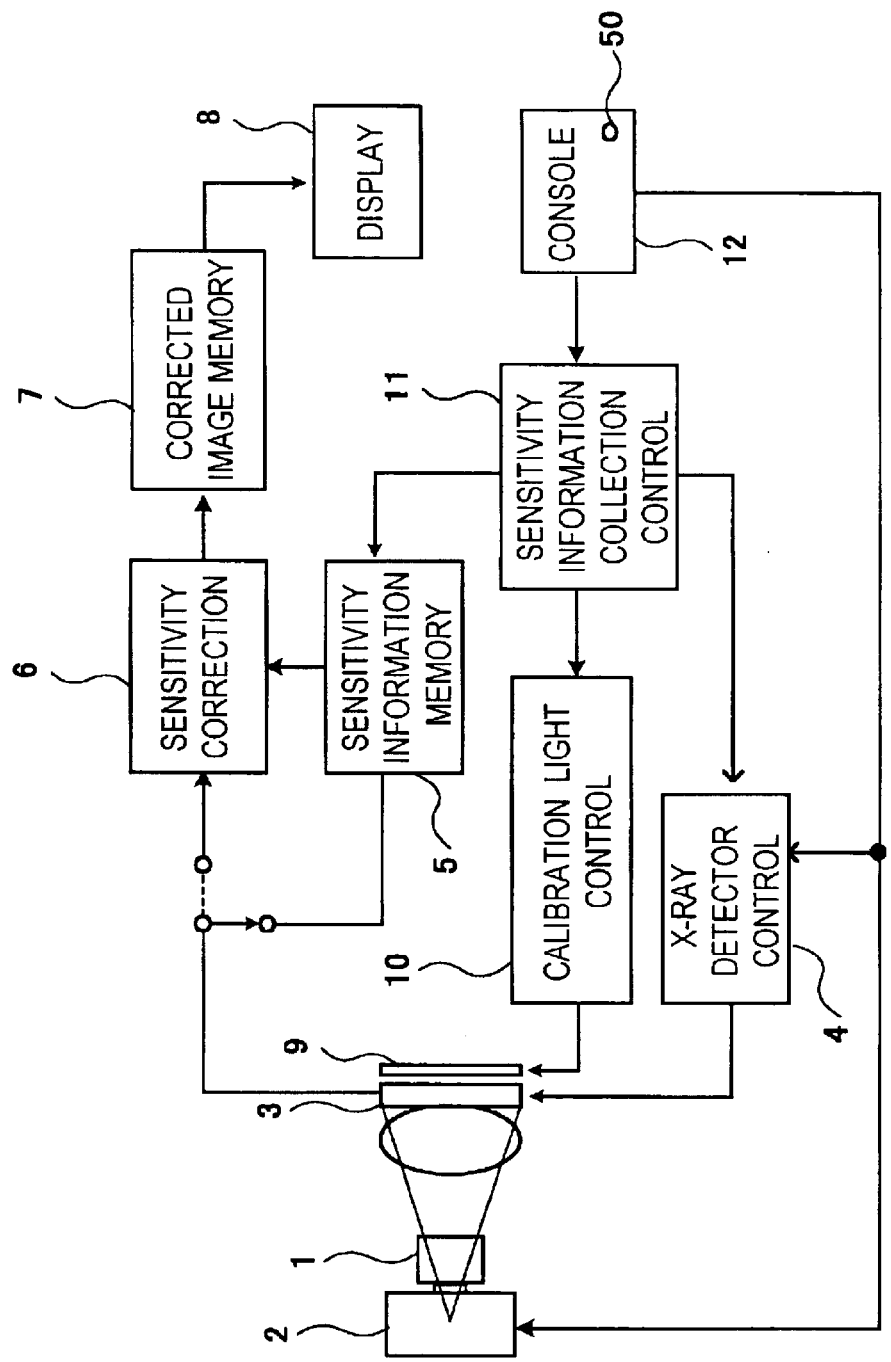
FIG. 1 is a schematic block diagram of an x-ray image diagnosis apparatus representing a first embodiment of the present invention.

FIG. 1 is a schematic block diagram of an x-ray image diagnosis apparatus representing the first embodiment of the present invention.

In FIG. 1, the x-ray image diagnosis apparatus representing the first embodiment of the present invention is provided with an x-ray source 2 which irradiates x-rays on to a subject 1, a two dimensional flat x-ray detector 3 which is disposed facing the x-ray source 2 and detects x-rays transmitted through the subject 1, and an x-ray detector control means 4 which controls read out of image information outputted from the flat x-ray detector 3.

Further, the x-ray image diagnosis apparatus is further provided with a sensitivity information memory means 5 which memorizes outputs from respective channels of the flat x-ray detector 3 as sensitivity information, a sensitivity correction means 6 which performs sensitivity correction of the image information read out from the flat x-ray detector 3 by making use of the sensitivity information memorized in the sensitivity information memory means 5, a correction image memory means 7 which memorizes the image information sensitivity-corrected by the sensitivity correction means 6, and a display means 8 which displays the image information memorized in the correction image memory means 7.

Further, the x-ray image diagnosis apparatus is further provided with a calibration light irradiation means 9 which is disposed at the opposite side of the x-ray source 2, while sandwiching the flat x-ray detector 3 therewith, and irradiates light beams on to photo diode arrays located inside the flat x-ray detector 3, a calibration light control means 10 which controls the calibration light irradiation means 9 so as to irradiate light beams inside the flat x-ray detector 3 during the sensitivity information collection period, a sensitivity information collection control means 11 which performs control of reading out calibration light signals being received from the flat x-ray detector 3 for collecting the sensitivity information following the light beam irradiation from the calibration light irradiation means 9 as well as causes to memorize the information read out from the flat x-ray detector 3 in the sensitivity information memory means 5 as the sensitivity information, and a console 12 which sends a signal for starting the collection of the sensitivity information to the sensitivity information collection control means 11 by an operator.

Now, an operation of collecting sensitivity information in the x-ray image diagnosis apparatus representing the first embodiment of the present invention will be explained.

The collection of the sensitivity information for respective channels in the flat x-ray detector 3 which is used for sensitivity correction of the image read out from the flat x-ray detector 3 during x-ray irradiation is started by sending the signal of starting the sensitivity information collection from the console 12 to the sensitivity information collection control means 11.

The sensitivity information collection control means 11 sends an irradiation start signal of the calibration light beams to the calibration light control means 10, and the calibration light control means 10 controls the calibration light irradiation means 9 so that the light beams with a desired intensity are irradiated on to the photo diode arrays disposed inside the flat x-ray detector 3.

Herein, the desired intensity of light beams irradiated inside the flat x-ray detector 3 is one which is sufficient for the sensitivity correction means 6 to obtain sensitivity information for performing sensitivity correction, and the light intensity can be modified by an operator from the console 12 based on the sensitivity information memorized in the sensitivity information memory means 5.

Figure 2:
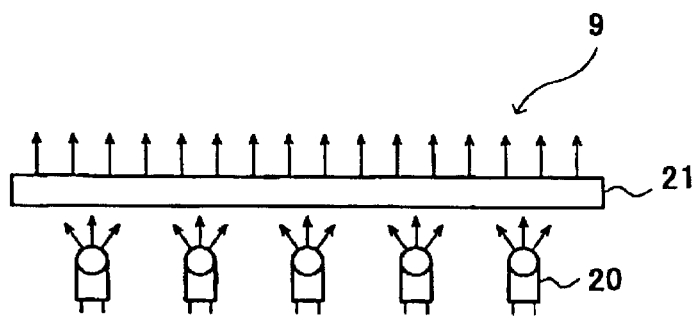
FIG. 2 is a schematic view for explaining the operation of a calibration light irradiation means.

In FIG. 2, when the irradiation start signal of the calibration light beams is sent from the calibration light control means 10 to the calibration light irradiation means 9, diodes 20 which emit light beams irradiate the light beams on to a diffusive plate 21 constituted, for example, by a glass plate of which surface is roughened.

Then, the light beams sufficiently diffused by the diffusive plate 21 are caused to make incident on to the photo diode arrays in the flat x-ray detector 3.

Figure 3:
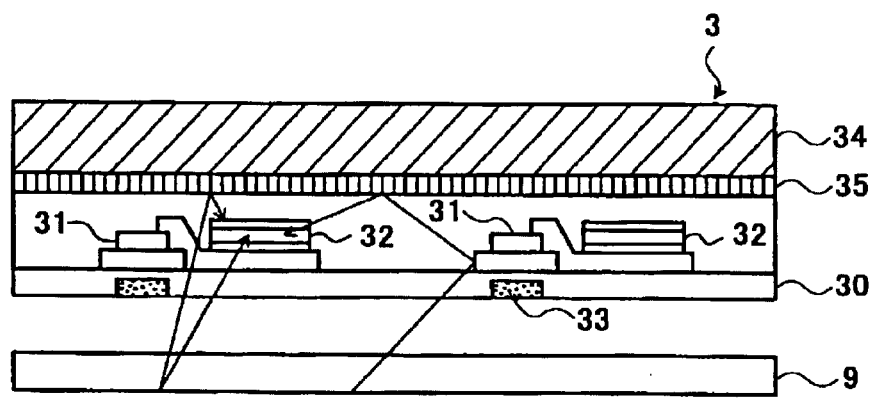
FIG. 3 is a schematic view for explaining a manner of light beams propagation in to a flat x-ray detector from the calibration light irradiation means.

FIG. 3 is a schematic view for explaining a manner of light beam propagation from the calibration light irradiation means 9 in to the flat x-ray detector 3 in the x-ray image diagnosis apparatus.

In FIG. 3, the flat x-ray detector 3 is constituted by disposing on a circuit substrate 30 plural switching elements 31 such as TFTs (Thin Film Transistors) and photo diodes 32 such as amorphous silicon.

Although it is possible to use semiconductor detecting elements such as photo transistors in place of the photo diodes 32, the photo diodes 32 are suitable for the flat x-ray detector 3 having the above referred to structure, because the structure of the photo diodes 32 is simple and assembling thereof in to the flat x-ray detector 3 can be performed easily.

Further, the plural switching elements 31 are respectively connected to data read out lines 33 of image information and via the data read out lines 33 the image information of the flat x-ray detector 3 is outputted.

In order to convert incident x-rays which have transmitted through the subject 1 and are irradiated on to the flat x-ray detector 3 into light beams, in particular, in to green light which is to be detected by the photo diodes 32, a scintillator 34 is constituted, for example, by CsI:Tl (Thallium doped Cesium Iodide scintillator).

The light beams irradiated from the calibration light irradiation means 9 are reflected and diffused by a reflection and diffusion plate 35 which is disposed between the scintillator 34 and the circuit substrate 30 including the switching elements 31, photo diodes 32 and data read out lines 33, thereafter, the light beams are received by the photo diodes 32.

Further, even with a structure with the scintillator 34 alone by omitting the reflection and diffusion plate 35, it is possible to reflect and diffuse the light beams from the calibration light irradiation means 9.

Herein, the calibration light irradiation means 9 is constituted by diodes 20 which emit green light, in that, light beams having wavelength of 420 nm~680 nm, in particular, light beams having wavelength of 530 nm.

Thereby, the light beams irradiated from the calibration light irradiation means 9 work in place of the x-rays which are converted by the scintillator 34 in to light beams and are received by the photo diodes 32.

In the above manner through memorizing the calibration light received signals outputted from the flat x-ray detector 3 as the sensitivity information in the sensitivity information memory means 5, the sensitivity information of the flat x-ray detector 3 can be collected without irradiating x-rays onto the flat x-ray detector 3.

With regard to the sensitivity information collection, plural sensitivity information collection modes, for example, a mode in which the sensitivity information of the flat x-ray detector 3 is automatically collected at the time of the power source start-up of the x-ray image diagnosis apparatus or another mode in which the sensitivity information of the flat x-ray detector 3 is collected immediately before or after respective x-ray image taking, are set in advance at the sensitivity information collection control means 11, and one of such modes is selected in advance from the console 12 based on the use environment of the x-ray image diagnosis apparatus. A button 50 on the console 12 is a button which causes to omit or interrupt the sensitivity information collection of the flat x-ray detector 3 at the time of immediate x-ray image taking for an emergency case. When the button 50 is pressed once again thereafter, the sensitivity information collection mode of the flat x-ray detector is restored to one set immediately before.

Further, during a sensitivity information collecting operation of the flat x-ray detector 3 according to the present embodiment, an indicator which was operated at the time during a conventional sensitivity information collection using x-rays to indicate an x-ray exposure state is rendered inoperative, instead of the conventional indicator, an indicator which shows a sensitivity information collecting operation using light beams is rendered operative.

As has been explained above, the first embodiment of the present invention is constituted in such a manner that at the opposite side from the x-ray irradiation in the flat x-ray detector 3 the calibration light irradiation means 9 for irradiating calibration light beams onto the flat x-ray detector 3 is disposed, and the sensitivity information of the respective photo diodes 32 with respect to the calibration light beams from the calibration light irradiation means 9 is obtained.

Accordingly, an x-ray image diagnosis apparatus, which permits collection of the sensitivity information for performing sensitivity correction of the respective channels without irradiating x-rays on to the flat x-ray detector, is realized.

In the above embodiment, due to influences of the structural bodies inside the flat x-ray detector 3 such as the switching elements 31, the photo diodes 32 and the data read out lines 33, it is possible that amount of the diffusive light from the reflection and diffusion plate 35 is not uniform for all of the photo diodes 32.

In order to countermeasure such instance, it may be preferable to provide a mechanism to correct such non-uniform amount of the diffusion light.

Figure 4:
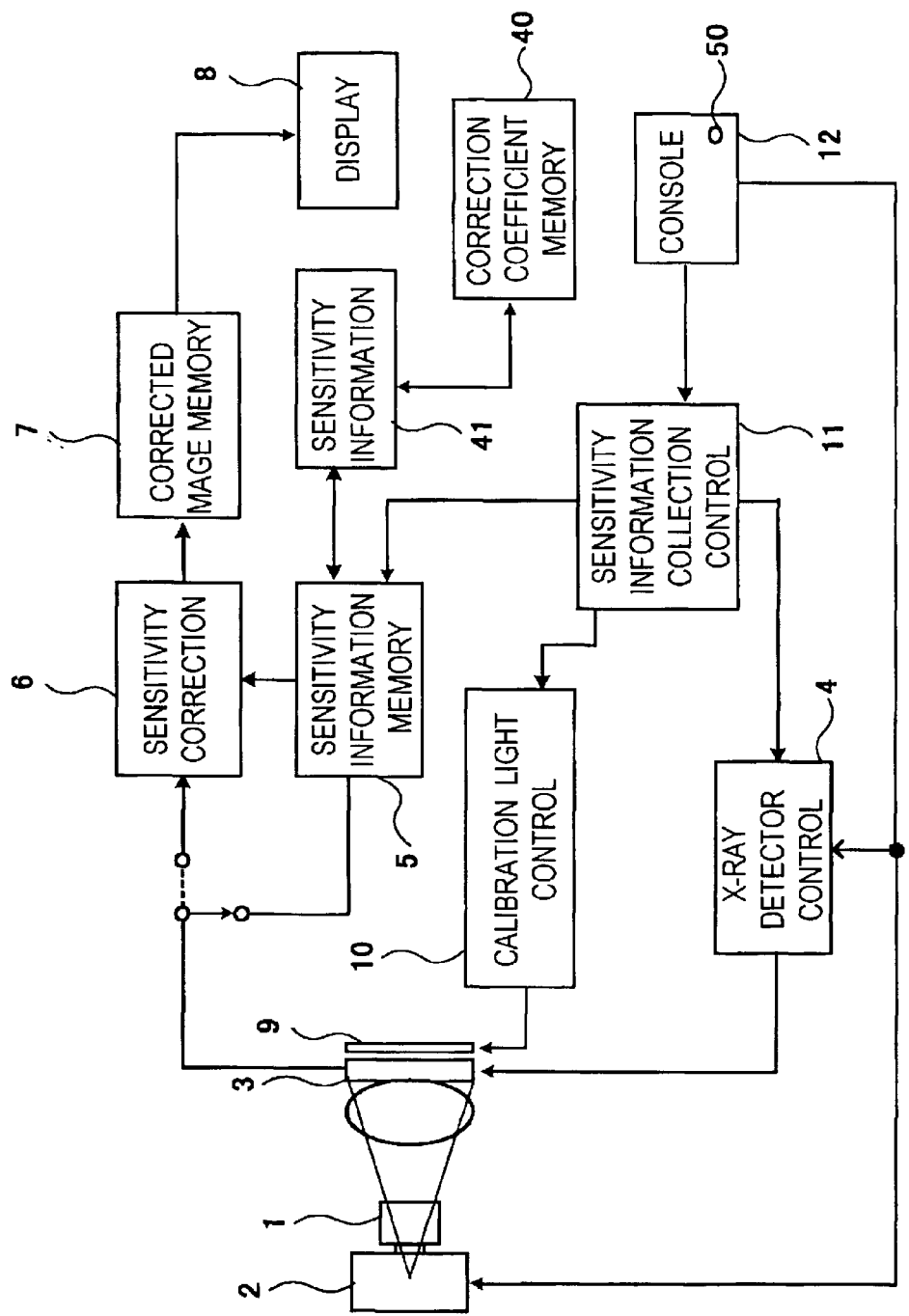
FIG. 4 is a schematic view of an x-ray image diagnosis apparatus representing a second embodiment of the present invention; and, FIG. 5 is a schematic view for explaining a manner of light beams propagation inside the flat x-ray detector from the calibration light irradiation means in a third embodiment of the present invention.

FIG. 4 is a schematic diagram of an x-ray image diagnosis apparatus representing a second embodiment of the present invention, which is provided with the above referred to non-uniform diffusion light amount correction mechanism.

In FIG. 4, the constitutional elements having the same functions as in FIG. 1 are denoted by the same reference numerals and the explanation thereof is omitted.

In FIG. 4, the x-ray image diagnosis apparatus representing the second embodiment is provided with a correction coefficient memory means 40 which memorizes correction coefficients for performing correction due to the non-uniformity of the diffusion light amount with regard to the sensitivity information memorized in the sensitivity information memory means 5 and a sensitivity information correction means 41 which performs the correction due to the irradiation light amount non-uniformity of the sensitivity information by making use of the correction information of the diffusion light amount memorized in the correction coefficient memory means 40.

Now, an operation of collecting sensitivity information in the x-ray image diagnosis apparatus of the second embodiment will be explained.

Under a condition where no subject 1 is exists between the x-ray source 2 and the flat x-ray detector 3, when a signal for determining the diffusion light amount non-uniformity correction coefficient is sent from the console 12 to the x-ray source 2 and the x-ray detector control means 4, the x-ray source 2 irradiates x-rays on to the flat x-ray detector 3 as well as the output signal from the flat x-ray detector 3 is memorized in the sensitivity information memory means 5 as corrected sensitivity information by x-rays through control of the x-ray detector control means 4.

Herein, the collection of the sensitivity information corrected by the x-rays is performed only when determining the diffusion light amount non-uniformity correction coefficient, for example, only once at the time when the x-ray image diagnosis apparatus of the present invention is installed and adjusted, in other words, at the time when such operation never disturbs the operator.

Subsequently, a signal for starting the sensitivity information collection by the light beams is sent from the console 12 to the sensitivity information collection control means 11 and according to the same sequence as in the first embodiment as shown in FIG. 1, sensitivity information by light beams is memorized in the sensitivity information memory means 5.

The sensitivity information correction means 41 determines ratios of respective parameters between the sensitivity information by the x-rays and the sensitivity information by the light beams memorized in the sensitivity information memory means 5 and memorizes the determined result in the correction coefficient memory means 40 as the diffusion light amount non-uniformity correction coefficient.

Thereafter, when the sensitivity information by light beams is memorized in the sensitivity information memory means 5 according to the same sequence as in the first embodiment, the sensitivity information correction means 41 performs correction of the sensitivity information by making use of the diffusion light amount non-uniformity correction coefficient memorized in the correction coefficient memory means 40 and rewrites the sensitivity information in the sensitivity information memory means 5.

As has been explained above, according to the second embodiment of the present invention, the same advantages as in the first embodiment is obtained, in addition, even when the amount of the diffusion light from the reflection and diffusion plate 35 is not equal to all of the photo diodes 32 due to the structural bodies in the flat x-ray detector 3, difference in diffusion light amount between the x-ray irradiation and the light beam irradiation can be corrected by the sensitivity information correction means 41.

Thereby, an x-ray image diagnosis apparatus provided with the correction mechanism, which permits to obtain accurate sensitivity information of the respective channels in the flat x-ray detector 3, can be realized.

Figure 5:
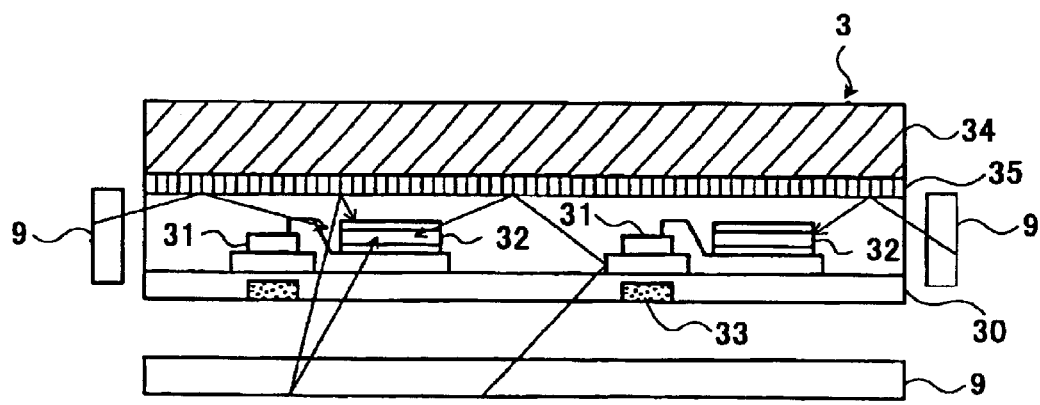

FIG. 5 is a view for explaining a manner of light beam propagation in to the flat x-ray detector from the calibration light irradiation means 5 according to a third embodiment of the present invention.

In the third embodiment, an arrangement of plural calibration light irradiation means 9 is exemplified so as to substantially uniformalize the diffusion light from the reflection and diffusion plate 35 to all of the photo diodes 32.

In the third embodiment, the correction coefficient memory means 40 and the sensitivity information correction means 41 in the second embodiment as shown in FIG. 4 can be omitted.

Since the other constitution of the present embodiment is the same as in the embodiments as shown in FIGS. 1 and 4, the illustration and explanation thereof are omitted.

In FIG. 5, other than the back side of the flat x-ray detector 3 the calibration light irradiation means 9 are disposed at the side faces thereof. Thus, light beams are irradiated from the calibration light irradiation means 9 at the back side of the flat x-ray detector 3 as well as from the calibration light irradiation means 9 at the side faces thereof in to the flat x-ray detector 3.

Thereby, the non-uniformity of the amount of diffused light received by the photo diodes 32, in particular, the amount of light received by photo diodes 32 disposed at end portions in the flat x-ray detector 3 and the amount of light received by photo diodes 32 disposed at the center portion thereof can be substantially equalized.

Herein, the amount of light beams irradiated from the calibration light irradiation means 9 disposed at the back side and the side faces are separately set by the calibration light control means 10.

As has been explained above, according to the third embodiment the same advantages as in the second embodiment can be obtained.

Further, although the x-ray image diagnosis apparatus according to the embodiments of the present invention have been explained with reference to the drawings, the present invention is not limited to the embodiments and the present invention can, of course, be practiced by properly modifying the same within the gist of the present invention.

For example, in the embodiments, although the two dimensional flat x-ray detector is exemplified, the present invention can be applied to an x-ray detector formed by arranging x-ray detecting elements in one dimension.

Still further, the embodiments exemplified that the correction image memory means 7 and the sensitivity information memory means 5, further the correction coefficient memory means 40 are constituted independently, however, they can be constituted in a common memory means.

Further, in the embodiment shown in FIG. 5 the calibration light irradiation means 9 are in addition disposed at the side faces so as to substantially equalize the amount of the diffusion light from the reflection and diffusion plate 35 on to all of the photo diodes 32, however, as an alternative, while disposing the calibration light irradiation means 9 only at the back side, and when the light emitting intensity of the calibration light irradiation means 9 disposed at the back side is adjusted in such a manner that the intensity is increased from the center portion toward the end portions, the amount of the diffusion light from the reflection and diffusion plate 35 can be substantially equalized for all of the photo diodes 32.

Still further, in the embodiments, the diodes 20 were used for the light emitting means in the calibration light irradiation means 9, however, the light emitting source is not limited to the light emitting diodes, and any light emitting means which emit light beams having wavelength in a range of 420 nm~680 nm can be used.

Still further, the ones irradiated on to the photo detection elements in the x-ray detector for calibration in place of the conventional x-rays can be any waves having comparable energy as that of the conventionally irradiated x-rays and are not limited to the light beams.

Still further, CsI:Tl is used for the scintillator 34, however, the same is constituted by other members, the wavelength of the light emitting source is not limited to the range of 420 nm~680 nm, ones having wavelength in a range from ultraviolet to infrared can be used.

Still further, in the embodiments, the calibration light irradiation means 9 is disposed at the opposite side from the x-ray source 2 with respect to the flat x-ray detector 3, however, if the same is disposed at a position permitting light beam irradiation on to the photo detection element arrays, the calibration light irradiation means 9 can be disposed at any positions.

According to the present invention, an x-ray image diagnosis apparatus, which permits collection of the sensitivity information for performing sensitivity correction of the respective channels in the flat x-ray detector without irradiating x-rays thereon, can be realized.

Accordingly, it is unnecessary to irradiate x-rays on to the flat x-ray detector at the time other than the image taking of the subject, therefore, a possible x-ray exposure to the operator in association with the sensitivity information collection can be avoided, and further, the preparation works for an inspection in the inspection room at the time of the sensitivity information collection are not restricted, therefore, after the sensitivity information collection, an image taking can be performed immediately.

What is claimed is:

1. An x-ray image diagnosis apparatus, comprising an x-ray source which irradiates x-rays on to a subject, a flat x-ray detector which is disposed facing the x-ray source and includes photo detection elements for converting x-rays transmitted through the subject into light beams and detecting the same, an x-ray detector control means which controls read out of image information outputted from the flat x-ray detector, a sensitivity information memory means which memorizes the sensitivity information outputted from the flat x-ray detector, and a sensitivity correction means which performs sensitivity correction of the image information read out from the flat x-ray detector by making use of the sensitivity information memorized in the sensitivity information memory means, further comprising means for irradiating light beams on to the photo detection elements in the flat x-ray detector in place of x-rays, and means for memorizing the output from the flat x-ray detector caused by the light beam irradiation in the sensitivity information memory means as the sensitivity information.

2. An x-ray image diagnosis apparatus according to claim 1, further comprising a correction coefficient memory means which memorizes correction coefficients for performing correction of the sensitivity information memorized in the sensitivity information memory means and a sensitivity information correction means which performs correction of the sensitivity information memorized in the sensitivity information memory means by making use of the correction coefficients memorized in the correction coefficient memory means.

3. An x-ray image diagnosis apparatus comprising, an x-ray source which irradiates x-rays on to a subject;

a flat x-ray detector which is disposed facing the x-ray source and includes photo detection element arrays for converting x-rays transmitted through the subject and detecting the same;

a flat x-ray detector control means which controls read out of image information of the subject outputted from the flat x-ray detector;

a calibration light irradiation means which irradiates sensitivity measurement use light beams on to the respective photo detection elements in the flat x-ray detector;

a sensitivity information memory means which memorizes the amount of received light from the calibration light irradiation means as sensitivity information of the respective photo detection elements in the flat x-ray detector; and a sensitivity correction means which performs sensitivity correction of the image information of the subject read out from the flat x-ray detector by making use of the sensitivity information memorized in the sensitivity information memory means.

4. An x-ray image diagnosis apparatus according to claim 3, wherein the calibration light irradiation means is arranged at the back and both sides of the flat x-ray detector.

5. An x-ray image diagnosis apparatus according to claim 3, wherein the calibration light irradiation means is arranged at the back of the flat x-ray detector, and the intensity of the irradiation light at the both end portions thereof is set larger than that at the center portion thereof.

6. An x-ray image diagnosis apparatus according to claim 3, further comprising a sensitivity information correction means which determines sensitivity error due to difference between the sensitivity measurement use irradiation light distribution for the respective photo detection elements in the flat x-ray detector by the calibration light irradiation means and the irradiation light distribution for the respective photo detection elements in the flat x-ray detector based on x-ray irradiation from the x-ray source.

7. An x-ray image diagnosis apparatus according to claim 3, further comprising means for temporarily omitting the operation of the calibration light irradiation means.

8. An x-ray image diagnosis apparatus, comprising an x-ray source which irradiates x-rays on to a subject, a flat x-ray detector which is disposed facing the x-ray source and includes photo detection elements for converting x-rays transmitted through the subject into light beams and detecting the same, an x-ray detector control means which controls read out of image information outputted from the flat x-ray detector, a sensitivity information memory means which memorizes the sensitivity information outputted from the flat x-ray detector, and a sensitivity correction means which performs sensitivity correction of the image information read out from the flat x-ray detector by making use of the sensitivity information memorized in the sensitivity information memory means, further comprising means for irradiating waves having comparable energy as that of the x-ray irradiation on to the photo detection elements in the flat x-ray detector in place of x-rays, and means for memorizing the output from the flat x-ray detector caused by the wave irradiation in the sensitivity information memory means as the sensitivity information.

* * * * *